United States Patent [19]
Brown et al.

[11] 4,192,784
[45] Mar. 11, 1980

[54] HYDROPHILIC COPOLYMERS, THEIR PREPARATION AND THEIR USE IN SEPARATION TECHNIQUES

[75] Inventors: Eric Brown, Le Mans; Egisto Boschetti, Chatou; Monique M. Corgier, Saint Quen; Joël Touet, Le Mans, all of France

[73] Assignee: Mar-Pha Societe d'Etudes et d'Exploitation de Marques, Paris, France

[21] Appl. No.: 873,026

[22] Filed: Jan. 27, 1978

[30] Foreign Application Priority Data

Jan. 28, 1977 [FR] France .................. 77 02391

[51] Int. Cl.$^2$ .................. C08L 89/00; C08L 3/00; C08F 20/54
[52] U.S. Cl. .................. 260/8; 260/17.4 SG; 260/17.4 ST; 260/29.6 TA; 260/29.6 H; 521/52; 521/149; 525/198; 525/328; 525/336; 525/355; 525/377; 526/88; 526/217; 526/304; 526/310; 526/909; 428/407; 428/474
[58] Field of Search .................. 526/304, 310, 88, 909; 260/8, 17.4 SG, 17.4 ST, 29.6 TA, 29.6 H; 521/52, 149; 525/198, 328, 336, 377; 428/407, 474

[56] References Cited

U.S. PATENT DOCUMENTS

| | | | |
|---|---|---|---|
| 3,591,387 | 7/1971 | Brust et al. | 526/304 |
| 3,658,734 | 4/1972 | Petitt | 260/17.4 ST |
| 3,733,196 | 5/1973 | Abel et al. | 96/94 R |
| 3,785,855 | 1/1974 | Shusaman et al. | 427/379 |
| 3,936,441 | 2/1976 | Holst et al. | 260/17 A |
| 4,025,703 | 5/1977 | Pornin et al. | 526/30 X |
| 4,037,035 | 7/1977 | Blanc et al. | 526/304 |
| 4,045,239 | 8/1977 | Hammer et al. | 260/8 |
| 4,048,377 | 9/1977 | Boschetti et al. | 260/17.4 SG |
| 4,101,461 | 7/1978 | Strop et al. | 526/49 |

OTHER PUBLICATIONS

Brown, et al., Tetrahedron Letters No. 6, pp. 357–358 (1975).

*Primary Examiner*—Herbert J. Lilling
*Attorney, Agent, or Firm*—Beveridge, DeGrandi, Kline & Lunsford

[57] ABSTRACT

Water-insoluble, tridimensional cross-linked random copolymers, which contain in copolymerized form:
(a) 25% to 98% by weight of N-[tris(hydroxymethyl)methyl]acrylamide or N-[tris(hydroxymethyl)methyl]methacrylamide or a mixture of these two compounds;
(b) 2% to 50% by weight of one or more monomers having several polymerizable ethylenic double bonds and one or more hydroxy groups, and free from $NH_2$ or COOH groups; and
(c) 0% to 50% by weight of one or more monomers having a polymerizable ethylenic double bond and one or more amino or carboxy groups. These copolymers may be used, in the form of aqueous gels, as supports in techniques of separation such as gell permeation chromatography and in techniques of immobilization of natural substances.

11 Claims, No Drawings

HYDROPHILIC COPOLYMERS, THEIR PREPARATION AND THEIR USE IN SEPARATION TECHNIQUES

BACKGROUND OF THE INVENTION

Field of the Invention

The present invention relates to new hydrophilic copolymers, processes for their preparation and their use, in the form of aqueous gels, in separation techniques, such as gel permeation chromatography (also called gel filtration), and in techniques of immobilization of natural substances, especially proteins and in particular enzymes.

Gel permeation chromatography is a current method of fractionation and separation of molecules according to their size. Molecules of a size greater than the largest pores of the gel are displaced by the mobile liquid phase, although molecules of a smaller size penetrate more or less deeply into the pores of the gel, which constitutes the stationary phase, and are then more or less retained. If then a liquid phase, in which a sample containing molecules of different sizes has been injected, is made to circulate on a column filled with gel, the speed of migration of these molecules towards the bottom of the column will vary from one molecule to another and the molecules will then be separated.

The principal hydrogels used at present as supports in the techniques described above are on the one hand gels of natural polysaccharides possibly cross-linked (agarose gels, dextran gels known under the trademark Sephadex) and, on the other hand, gels of synthetic or semisynthetic polymers such as, for example, the gels of polyacrylamide or the polyacrylamide-agarose mixed gels. These supports are not free of defects. The gels of polyacrylamide or polyacrylamide-agarose are chemically unstable in a basic medium owing to hydrolysis of the amide groups into carboxylic acid groups, which limits their field of use. Certain gels of dextran have moderate mechanical properties, and hence it is impossible to make columns thereof having a relatively high and constant rate of flow. Finally, the agarose gels have a poor resistance to heat and to agents for weakening the hydrogen linkages (urea, guanidine, etc.), and further, like all gels of natural origin, are very sensitive to attack by bacteria or certain enzymes.

Because of the defects described above, it has been proposed to replace the gels set forth above by gels of hydrophilic copolymers of N-[tris(hydroxymethyl)-methyl]methacrylamide and of N,N'-ethylene-bis-methacrylamide or N,N'-methylene-bis-acrylamide (cross-linking agent) (cf. Tetrahedron Letters No. 6, pgs. 357–358, 1975). However, to obtain homogeneous gels, therefore transparent, of such copolymers is difficult since, during the polymerization, there is formed, especially in the case of high concentrations of cross-linking agent, homopolymers of N,N'-ethylene-bis-methacrylamide or N,N'-methylene-bis-acrylamide, which form white precipitates in the gel.

SUMMARY OF THE INVENTION

There have now been found, according to the present invention, new very hydrophilic copolymers which can be easily obtained in the form of aqueous homogeneous gels and which are capable of replacing advantageously, in their applications, both the highly cross-linked gels, such as the dextran gels, and the macroreticulated or highly cross-linked gels, such as the agarose gels.

DESCRIPTION OF THE PREFERRED EMBODIMENTS

The copolymers according to the present invention are three-dimensional cross-linked random copolymers, insoluble in water, which contain in copolymerized form:

(a) 25% to 98% by weight of N-[tris(hydroxymethyl)methyl]acrylamide or N-[tris(hydroxymethyl)-methyl]methacrylamide, or a mixture of these two compounds;

(b) 2% to 50% by weight of one or more monomers containing several polymerizable ethylenic double bonds and one or more hydroxy groups, and free of NH$_2$ or COOH groups, and (c) 0% to 50% by weight of one or more monomers containing a polymerizable ethylenic double bond and one or more amino or carboxy groups.

The monomers (a) are known products. They have been described, with their methods of preparation, in various publications (cf. for example, Jedlinski and Paprotny, Roczniki Chemii, Ann. Soc. Chim. Polonorum, 1966, 40, pp. 1487–1493; Tetrahedron Letters No. 6, 1975, pp. 357–358).

The monomers (b), which are cross-linking agents, correspond preferably to one of the general formulae (I) or (II) below:

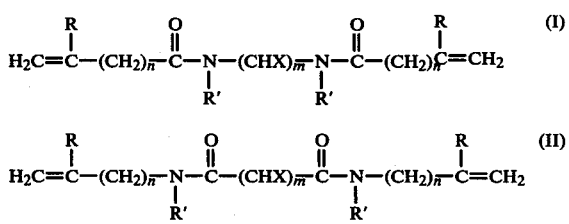

in which R is a hydrogen atom or a methyl group, R' is a hydrogen atom or a hydroxymethyl group; X is a hydrogen atom or an OH group, n and m are whole numbers from 0 to 6; with the restriction that X and R' cannot be simultaneously hydrogen atoms.

Examples of monomers (b) include especially N,N'-diallyltartradiamide, N,N'-methylene-bis-hydroxymethylacrylamide and glyoxal-bis-acrylamide (also called N,N'-dihydroxyethylene-bis-acrylamide).

Examples of compounds (c) are, among others, N-[(N-acryloyl)-glycyl]glycine, N-[(N-methacryloyl)-glycyl]glycine, and N-acryloyl-ε-aminocaproic acid, N-acryloyl glycine and acrylamido glycolic acid.

Although the present invention relates to the whole of the copolymers defined above, it is more particularly related to those of these copolymers which contain, in copolymerized form, 50% to 98% by weight of monomers (a), the remaining 50% to 2% being formed by one or more monomers (b), and most particularly to those which contain 50% to 98% by weight of N-[tris-(hydroxymethyl)-methyl]acrylamide, the complement to 100% being formed by one or more monomers (b).

The cross-linked hydrophilic copolymers according to the present invention can be prepared, according to known processes, by free radical polymerization of the various monomers in aqueous solution. The polymerization is effected at a temperature from 0° C. to 100° C., preferably from 40° C. to 60° C., and in the presence of the usual initiators used in free radical polymerization. Examples of such initiators are redox systems such as N,N,N',N'-tetra-methyl-ethylenediamine (TEMED)-+alkali metal persulfate or dimethylaminopropionitrile+alkali metal persulfate, the organic peroxides such as benzoyl peroxide, and 2,2'-azo-bis-isobutyronitrile. The total concentration of monomers [i.e. the concentration of monomers (a)+(b)+(c)] in the aqueous solutions subjected to the polymerization is generally from 20 g/l to 300 g/l and the percentage by weight of monomer (b) in the total monomers is from 2% to 50%.

The polymerization may be a block polymerization or an emulsion polymerization. In the case of block polymerization, the aqueous solution containing the various monomers and the initiator is subjected to a polymerization in a homogeneous phase. The block of aqueous gel obtained is then fractionated in grains, for example, by passing it through the meshes of a screen.

Emulsion polymerization, which is the preferred method of preparation since it provides directly the aqueous gel in the form of spherical granules of determined size, may be effected as follows:

An aqueous solution containing the various monomers is poured slowly into an organic liquid phase, non-miscible with water, maintained in agitation and possibly containing an emulsifying agent. The speed of stirring is regulated so as to obtain an emulsion of the aqueous phase in the organic phase having the desired size of droplets. The control of this size, and therefore the control of the stirring, is effected by examination under the microscope of samples taken from the emulsion. Once the speed of stirring is regulated, the initiator is introduced into the emulsion, which starts the polymerization. The latter is carried out to its end while maintaining the same conditions of agitation. The beads of aqueous gel thus obtained are washed with a solvent or a surface-active agent so as to remove any traces of organic phase, and then are washed with water.

As the liquid organic phase, there may be used vegetable oils (soya oil, arachis oil, sunflower seed oil, etc.) or mineral oils (paraffin oil, silicone oil) the products of fractional distillation of petroleum (benzene, toluene, etc.), chlorinated hydrocarbons (carbon tetrachloride, methylene chloride, etc.) and mixtures of these various compounds. The liquid organic phase may possibly contain an emulsifying agent such as the products known commercially as "Spans" or "Tweens" in a concentration of 0.1% to 4% by volume.

The beads of aqueous gel obtained by the process of emulsion polymerization have a particle diameter which varies from 10 μm to 600 μm according to the operating conditions.

The aqueous gels obtained by one of the processes described above may be kept in suspension in water or in an aqueous buffer solution, in the presence of traces of a bacteriostatic substance, such as, for example, sodium azide. A concentration of 0.02% of sodium azide is sufficient to ensure preservation.

The aqueous gels may also be dried by conventional processes (lyophilization, treatment with an organic solvent miscible with water, etc.). The copolymers are thus obtained in the form of a white powder, rehydratable at the moment of use. The rehydration is effected by mere contact with water or an aqueous buffer solution. The copolymer powders represent a very convenient form for storage, since they occupy a very small volume and can be kept indefinitely without addition of preservatives and bacteriostatic agents. The aqueous gels may contain from 2% to 6% by weight of copolymer according to the present invention, the remainder being formed by water of hydration.

The copolymers according to the invention are thermally stable (they resist temperatures reaching 120° C. to 130° C.) and are insensitive to bacterial or enzymic attack. In addition, they are chemically stable in the presence of distinctly acidic (pH 2) or basic (pH 13) aqueous solutions, which enables their use in a very wide pH field.

The copolymers according to the present invention may be advantageously used, in the form of aqueous gels, as supports in techniques of gel permeation chromatography operating in an aqueous medium or in a $H_2O$+organic solvent mixed medium. They allow to be separated, according to their size, components of mixtures of macromolecular substances and especially the components of protein mixtures. The properties of the gels (rigidity, fractionation field) depend on the total concentration of monomers in the aqueous solution subjected to the polymerization, the nature of the crosslinking agent (monomer b) and its percentage of the total monomers, and also the conditions of polymerization. By varying these various parameters, a whole range of gels with diverse characteristics is obtained. These gels allow the separation of macromolecules of which the molecular weight ranges from 500 daltons up to several millions of daltons.

The copolymers according to the present invention may also be used, in the form of aqueous gels, as a support for immobilization or the affinity chromatography of biological macromolecules, such as, for example, proteins and in particular enzymes. For this purpose the copolymers are previously activated; i.e. the primary alcohol groups of the copolymers are converted, by chemical reaction with bi- or poly-functional compounds, into groups capable of causing the attachment of the biological macromolecules on the support (for example, imidocarbonate groups). The copolymers according to the present invention are activated according to known methods (see on this subject British Pat. Nos. 1,183,257; 1,343,703 and DOS No. 2,061,008). As examples of activation agents which may be used are cyanogen bromide in alkaline medium, glutaraldehyde, epoxide derivatives, such as epichlorhydrin or 1,4-butanediol diglycidyl ether, and the derivatives of 1,3,5-trichloro-2,4,6-triazine. The copolymers according to the invention lend themselves particularly well to activation by cyanogen bromide.

The immobilization, i.e. the attachment, of the proteins on to the aqueous gels of activated copolymer is effected according to conventional methods, for example, by stirring for several hours the beads of activated gel in an aqueous buffer medium containing the proteins to be fixed. At the end of the operation, the beads of gel, which have fixed the proteins at least partially, are separated and preserved in an adequate buffer medium.

As examples of proteins, which may thus be immobilized in the form of a combination with activated gels of copolymers according to the invention, may be mentioned arginase, invertase, glucose oxidase, urease, alkaline phosphatase, trypsin and chymotrypsin.

The copolymers according to the invention may be associated with natural, water-soluble and gelifiable, macromolecular products, such as, for example, agar-agar, agarose or gelatin, so as to obtain mixed gels having particular characteristics. Thus, in order to obtain particularly hard gels, a copolymer according to the invention will be associated with agarose. In these mixed gels the ratio by weight:

$$\frac{\text{gelifiable natural macromolecular product}}{\text{copolymer according to the invention}}$$

is $\leq 2$.

In order to prepare such mixed gels, the operation is as previously indicated, except that the desired quantity of gelifiable natural macromolecular product is introduced at the beginning into the aqueous solution of the monomers, this quantity corresponding to a concentration in general between 0.5 and 6% by weight in the aqueous solution. The natural macromolecular product is gelified inside the meshes of the copolymer when the reaction medium is cooled after the polymerization.

The following specific examples illustrate the invention without restricting it thereto.

EXAMPLE 1

Preparation of a copolymer N-[tris(hydroxymethyl)methyl]acrylamide/N,N'-diallyl-tartradiamide in the form of an aqueous gel, by block polymerization.

10 grams of N-[tris(hydroxymethyl)methyl]acrylamide and 1 gram of N,N'-diallyl-tartradiamide were dissolved in 100 ml. of demineralized water, contained in a vessel placed on a water-bath at 50° C. The solution was then filtered, degasified in vacuum and replaced on the water-bath at 50° C. The solution was gently stirred by means of a magnetic stirrer and 150 mg. of ammonium persulfate and 0.16 ml. of TEMED were introduced. At the end of a few minutes a slight heating of the reaction medium was observed, followed by gelling of the solution. A block of rigid and transparent aqueous gel was thus obtained. This block was fragmented into grains by passing it over a screen having meshes of 100 μm. The grains were washed and preserved in the selected buffer solution.

The homogeneous gel thus obtained may be used as support in gel permeation chromatography. Its field of fractionation extends from 2500 daltons to 300,000 daltons.

The gel may also be used, after activation, for immobilizing biological macromolecules.

EXAMPLES 2–4

The operation was as in Example 1, but using, for 100 ml. of demineralized water, the following quantities of monomers.

| Example | N-[tris(hydroxymethyl)methyl] acrylamide | N,N'-diallyl-tartradiamide |
|---------|------------------------------------------|---------------------------|
| 2 | 5 g. | 1 g. |
| 3 | 10 g. | 0.5 g. |
| 4 | 20 g. | 1 g. |

Homogeneous transparent gels were obtained with varied characteristics. The gel of Example 2 was not very compact, that of Example 3 was compact and that of Example 4 was very hard.

These gels may be used as supports in gel permeation chromatography or for the immobilization of biological macromolecules. The fields of fractionation of the gels of Examples 3 and 4 are respectively:
2500 daltons to 300,000 daltons (Example 3)
1000 daltons to 100,000 daltons (Example 4)

EXAMPLE 5

Preparation of a copolymer N-[tris(hydroxymethyl)methyl]acrylamide/glyoxal-bis-acrylamide in the form of beads of aqueous gel.

350 ml. of paraffin oil and 2 ml. of emulsifying agent known commercially as "Span-85" were introduced into a 700 ml. reactor. The mixture was stirred mechanically and heated to 55° C. In addition, 40 g. of N-[tris(hydroxymethyl)methyl]acrylamide and 4 g. of glyoxal-bis-acrylamide were dissolved in 200 ml. of water heated to 55° C. and 300 mg. of ammonium persulfate were added to this solution. The solution thus obtained was poured into the stirred paraffin oil. The speed of stirring was regulated so as to obtain a stable emulsion of which the droplets had a diameter of about 100 μm. At the end of 10 minutes of stirring, 0.32 ml. of TEMED were introduced into the emulsion and stirring was continued for a further 30 minutes.

The reaction medium was then cooled by addition of ice water, stirring was stopped and the mixture was allowed to stand for some hours. The supernatant oil phase was removed by suction and the beads of gel obtained, of diameter of about 100 μm, were recovered by decantation. These beads were washed by means of a 0.1% aqueous solution of Triton X - 100 in order to remove the oil residues, then with demineralized water until the detergent was totally eliminated. The beads can be preserved in water or in a suitable buffer solution. The homogeneous transparent aqueous gel thus obtained is very hard. It has a fractionation field which extends from 1500 to 50,000 daltons. It is particularly suitable for the operations of removing the salts of protein solutions on a column.

EXAMPLES 6–8

The operation was as in Example 5 but using for 200 ml. of water, the following quantities of monomers:

| Example | N-[tris(hydroxymethyl)methyl] acrylamide | glyoxal-bis-acrylamide |
|---------|------------------------------------------|------------------------|
| 6 | 10 g. | 1 g. |
| 7 | 20 g. | 2 g. |
| 8 | 40 g. | 2 g. |

Homogeneous transparent gels were obtained which can be used as support in gel permeation chromatography or for the immobilization of biological macromolecules. The fractionation field of the gel of Example 7 is 2500 daltons to 300,000 daltons.

EXAMPLE 9

This Example is given by way of comparison.

In the previous Examples 1, 2, 5, 6 and 7, the N,N'-diallyl-tertradiamide and the glyoxal-bis-acrylamide were replaced by N,N'-methylene-bis-acrylamide. Aqueous gels were obtained which were not transparent, therefore which were heterogeneous.

EXAMPLE 10

Preparation of a mixed gel containing agarose and a copolymer N-[tris(hydroxymethyl)methyl]acrylamide/glyoxal-bis-acrylamide.

The polymerization was effected as in Example 5, except that the paraffin oil was replaced by soya oil, 7 ml. of "Span 85" were used instead of 2 ml., and the aqueous solution poured into the oil contained for 200 ml. of water, 30 g. of N-[tris(hydroxymethyl)methyl]acrylamide, 3 g. of glyoxal-bis-acrylamide, 4 g. of agarose and 300 mg. of ammonium persulfate.

Once the polymerization had ended, the temperature of the emulsion was lowered progressively to 40° C., then the emulsion was cooled rapidly by addition of ice water. The supernatant oily phase was eliminated by suction and the beads of mixed gel obtained were separated, washed by means of a 0.2% aqueous solution of sodium laurylsulfate, then with demineralized water. The beads were preserved in suspension in water at 4° C. containing traces of a bacteriostatic agent, such as sodium azide.

The aqueous gel thus obtained is particularly hard and very suitable for chromatography with a high rate of flow. This gel is not thermostable and must be used at temperatures below 37° C.

EXAMPLE 11

Preparation of a copolymer N-[tris(hydroxymethyl)methyl]acrylamide/glyoxal-bis-acrylamide in dry form.

The beads of aqueous gel obtained in Examples 5 to 8 were put with water in a vessel provided at its bottom with an outlet to which had been applied a filter. The beads were maintained in suspension by continuous magnetic agitation. Ethyl alcohol was introduced continuously in the upper part of the vessel, the rate of introduction being regulated so as to be equal to the flow of water from the outlet at the base of the vessel. The beads in suspension were thus contacted with a medium increasingly more rich in ethanol. The water was thus driven away progressively from the interior of the beads and was replaced by the ethanol. When the operation was finished, the ethanol was replaced in its turn by acetone, then the acetone by ethyl ether following the same method. Finally, a gel soaked with ether was obtained which was dried under a current of air in a few minutes.

There was thus obtained, for 100 ml. of starting gel, about 5 to 20 g. of copolymer in the form of a fine powder made up of small spheres. This powder can be immediately rehydrated by mere contact with water and the particles again take their initial form. The behavior in chromatography of the rehydrated dried gel does not differ from that of the initial aqueous gel.

EXAMPLE 12

Application to the immobilization of enzymes.

5 ml. of the beads of aqueous gel obtained in Example 7 and 15 ml. of demineralized water were placed in a conical 20 ml. flask. The mixture was stirred and 4 ml. of an aqueous solution of cyanogen bromide containing 50 mg. cyanogen bromide per ml. were added. Stirring was continued while maintaining the pH at 11 by addition of a N solution of caustic soda. After stabilization of the pH, stirring was continued for a further 30 minutes, and the beads were filtered, washed rapidly with 100 ml. of a 0.1 M aqueous solution of sodium bicarbonate, then with a M solution of sodium chloride. The beads of activated gel thus obtained were then used for the fixation of the arginase.

The activated gel was placed in 10 ml. of a buffer medium maleate/$MnCl_2$ $5\times10^{-2}$ M, pH 7.2 containing 10 mg. of arginase at 15 units/mg. The suspension was agitated on a balancelle for 24 hours at 4° C. Then the beads were filtered, washed with 25 ml. of a M solution of sodium chloride and 25 ml. of demineralized water.

The activated gel-arginase derivative thus obtained was preserved in suspension in a maleate/$MnCl_2$ buffer $5\times10^{-2}$ M, pH 7.2.

The amount of enzyme fixed on the activated gel was determined indirectly by determining the enzyme remaining in the filtrate by the conventional method with the reagent of FOLIN (cf. LOWRY, et al., J. Biol. Chem., 1951, 193, 265). The enzymatic activity of the activated gel-arginase derivative was determined by the method of hydrolysis of arginine (J. J. HAGAN and R. D. DALLAM, Anal. Biochem. 1968, 22, 518).

The results obtained in two similar experiments are given in the following Table.

| Test | Mg. of arginase fixed per ml. of gel | % of arginase fixed on the activated gel | % of residual activity of the fixed arginase |
|---|---|---|---|
| 1 | 1.3 | 65% | 36% |
| 2 | 1.47 | 73.5% | 37% |

The percentage of residual activity, which expresses the enzymatic activity of the derivative, is defined by the formula:

$$100(M_1/M_3)$$

in which $M_3$ represents the mass of fixed enzyme and $M_1$ is the mass of native enzyme having the same activity as the mass of fixed enzyme.

EXAMPLE 13

Preparation of a copolymer N-[tris(hydroxymethyl)methyl]acrylamide/N,N'-dihydroxyethylene-bis-acrylamide/6-acrylamide hexanoic acid (or N-acryloyl-ε-aminocaproic acid) in the form of beads of aqueous gel.

The operation was as in Example 5, but replacing in the aqueous solution the 40 g. of N-[tris(hydroxymethyl)methyl]acrylamide and 4 g. of glyoxal-bis-acrylamide by 35.6 g. of N-[tris(hydroxymethyl)methyl]acrylamide, 4.0 g. of N,N'-dihydroxyethylene-bis-acrylamide and 0.4 g. of 6-acrylamido hexanoic acid. The aqueous solution was brought to a pH of 6 and the operation was followed up as in Example 5.

There was thus obtained, in the form of beads having a diameter between 30 and 250 μm, an aqueous gel containing 6 to 20 microequivalents (μeg) COOH per ml. of gel.

EXAMPLE 14

Preparation of a copolymer N-[tris(hydroxymethyl)methyl]methacrylamide/N,N'-dihydroxyethylene-bis-acrylamide/N-[(N-methacryloyl)glycyl]glycine in the form of beads of aqueous gel.

The operation was as in Example 5, but replacing in the aqueous solution the 40 g. of N-[tris(hydroxymethyl)methyl]acrylamide and the 4 g. of glyoxal-bis-acrylamide by 10.5 g. of N-[tris(hydroxymethyl)methyl]methacrylamide, 1.2 g. of N,N'-dihydroxyethylene-bis-acrylamide and 0.2 g. of N-[(N-methacryloyl)-glycyl]glycine.

There was, thus obtained, in the form of beads having a diameter between 30 and 250 μm, an aqueous gel containing 6 to 20 μeg COOH per ml. of gel.

What is claimed is:

1. Water-insoluble, tridimensional cross-linked random copolymers resulting from the free radical polymerization of a mixture of monomers containing:
   (a) 25% to 98% by weight of N-[tris(hydroxymethyl)methyl]acrylamide or N-[tris(hydroxymethyl)methyl]methacrylamide or a mixture of these two compounds;
   (b) 2% to 50% by weight of one or more monomers having two or several polymerizable ethylenic double bonds and one or more hydroxy groups, and free of $NH_2$ or COOH groups; and
   (c) 0% to 50% by weight of one or more monomers having one polymerizable ethylenic double bond and one or more amino or carboxy groups.

2. Copolymers as defined in claim 1 in which the monomers (b) correspond to one of the formula:

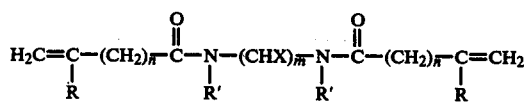

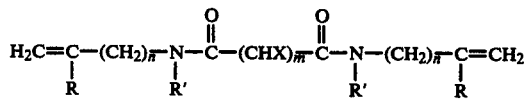

in which R is a hydrogen atom or a methyl group, R' is a hydrogen atom or a hydroxymethyl group, X is a hydrogen atom or an OH group, n and m are whole numbers from 0 to 6, with the proviso that X and R' are not simultaneously hydrogen atoms.

3. Copolymers as defined in claim 1 which contain, in polymerized form, 50% to 98% by weight of monomers (a), the complement to 100% being consituted by one or more monomers (b).

4. Copolymers as defined in claim 3 in which the monomer (a) is N-[tris(hydroxymethyl)methyl]acrylamide.

5. Copolymers as defined in claim 3 in which the monomer (b) is N,N'-diallyl-tartradiamide.

6. Copolymers as defined in claim 3 in which the monomer (b) is glyoxal-bis-acrylamide.

7. Copolymers as defined in claim 3 in which the monomer (b) is N,N'-methylene-bis-hydroxymethylacrylamide.

8. Aqueous gels which contain 2% to 60% by weight of a copolymer as defined in claim 1.

9. Aqueous gels as defined in claim 8, which are in the form of beads having a diameter of 10 μm to 600 μm.

10. Aqueous gels as defined in claim 8 which contain also a gelifiable natural macromolecular product, the ratio by weight $$\frac{\text{gelifiable natural macromolecular product}}{\text{copolymer}}$$

in the gel being less than or equal to 2.

11. Aqueous gels as defined in claim 10 in which the gelifiable natural macromolecular product is agarose, agar-agar or gelatin.

* * * * *